United States Patent [19]

Huang et al.

[11] Patent Number: 4,644,009
[45] Date of Patent: Feb. 17, 1987

[54] ARYL-ALKYL HETEROCYCLIC COMPOUNDS

[75] Inventors: Fu-chih Huang, Leonia, N.J.; Joseph Auerbach, Brooklyn, N.Y.

[73] Assignee: USV Pharmaceutical Corporation, Tuckahoe, N.Y.

[21] Appl. No.: 665,428

[22] Filed: Oct. 29, 1984

[51] Int. Cl.$^4$ .................. A61K 31/40; C07D 207/323
[52] U.S. Cl. ........................... 514/423; 514/427;
548/539; 548/540; 548/560; 548/562; 548/563;
549/72; 549/78; 549/498; 549/502
[58] Field of Search ............... 548/539, 540, 560, 562,
548/563; 514/423, 427

[56] References Cited

U.S. PATENT DOCUMENTS

| | | | |
|---|---|---|---|
| 2,171,159 | 8/1939 | McNally et al. | 548/539 X |
| 3,337,562 | 8/1967 | Pesson | 548/540 X |
| 3,655,693 | 4/1972 | Shen et al. | 548/560 X |
| 4,000,160 | 12/1976 | Bailey | 548/562 X |
| 4,347,185 | 8/1982 | Muchowski et al. | 548/539 X |
| 4,418,074 | 11/1983 | Moore | 548/539 X |

*Primary Examiner*—Joseph Paul Brust

[57] ABSTRACT

Provided are new compounds having valuable therapeutic activity. These compounds are of the formula:

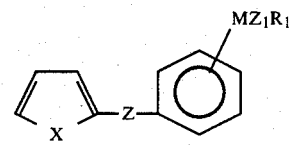

and salts thereof,
wherein
$X = O$, S or $NR_2$;
$Z = (CHR_3)_nC(R_3))OH)—$,

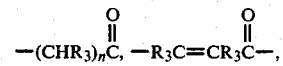

$—CH_3=CH_3CR_3(OH)—$, or $—(CHR_3)_{n'}$,
$M = —O—, —S—$, or

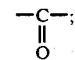

$Z_1$ is an alkylene chain of 0–5 carbon atoms in the principal chain and a total of 7 carbon atoms;
$R_1$ is H, phenyl, naphthyl or a sulfur, nitrogen or oxygen-heterocyclic ring;
$R_2$ is H, alkyl, aryl or aralkyl;
$R_3$ is H or $CH_3$;
$n = 0–5$; and
$n' = 1–5$.

8 Claims, No Drawings

ARYL-ALKYL HETEROCYCLIC COMPOUNDS

This invention relates to new chemical compounds which possess valuable therapeutic activity particularly as lipoxygenase inhibitors possessing anti-inflammatory and antiallergic properties.

The present new compounds are of the formula:

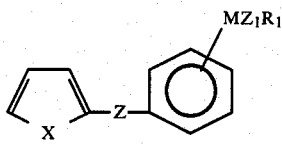

and salts thereof,
wherein
X=O, S or $NR_2$;
$Z=(CHR_3)_n C(R_3)(OH)—$,

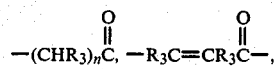

$—CR_3{=}CR_3CR_3(OH)—$, or $—(CHR_3)_{n'}—$,
M= —O—, —S—, or

$Z_1$ is an alkylene chain of 0-5 carbon atoms in the principal chain and a total of 7 carbon atoms;
$R_1$ is H, phenyl, naphthyl or a sulfur, nitrogen or oxygen-heterocyclic ring;
$R_2$ is H, alkyl, aryl or aralkyl;
$R_3$ is H or $CH_3$;
n=0-5; and
n'=1-5.

The heterocyclic rings exemplary of $R_1$ contain at least one oxygen, sulfur or nitrogen and include the so-called benzoheterocyclic rings. Exemplary heterocyclics include thiophene, pyrrole, pyridine, thiazole, piperazine, oxazole, benzofuran, quinoline, indole, benzothiophene, benzoxazole and similar heterocyclic rings as well as the N-oxides of the nitrogen heterocyclics. The preferred heterocyclics are quinoline and indole.

The heterocyclics representative of $R_1$, as well as those represented by the structure in formula I:

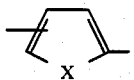

may be fully or partially saturated and include, for example, tetrahydrofuran, tetrahydrothiophene, tetra- and dihydropyrrole and the like. In addition, the said heterocyclics can also include the so-called benzoheterocyclics such as benzofuran, benzothiophene, indole, benzoxazole, and the like, as well as the dihydro derivatives thereof.

Compounds which are particularly preferred are those in which $R_1$ is phenyl or naphthyl. The alkylene chains of which $Z_1$ is representative are branched or normal chains of up to 5 carbon atoms in the normal or principal chain and a total of up to 7 carbon atoms. The branches in the alkylene chains are preferably methyl or ethyl groups.

The alkyl groups, either alone or within the various substituents defined hereinbefore are preferably lower alkyl which may be straight or branch-chain, and include methyl, ethyl, propyl, isopropyl, butyl, isobutyl, amyl, hexyl and the like.

The halo atoms in halo and trihalomethyl are Cl, Br, I and preferably F. The aryl groups are preferably phenyl and naphthyl.

The heterocyclic ring and phenyl ring of formula I, as well as the aryl groups, i.e., phenyl and the aryl group of arylalkyl, may be substituted with one or two substituents such as OH, alkoxy, phenoxy, benzyloxy, halogen, alkyl, carboxy, carbalkoxy, carboxamide, phenyl, alkylmercapto, trihalomethyl, formyl, nitro, amino, sulfamyl, nitrilo and similar such groups.

The preferred compounds of Formula I are those in which $R_1$ is phenyl or naphthyl, $Z_1$ contains up to three carbon atoms in the principal chain, n=0-3, n'=1-3 and M is 0.

The present new compounds are prepared by known methods from starting materials either known or readily preparable.

The following general procedure can be employed to produce compounds of formula I in which Z is:

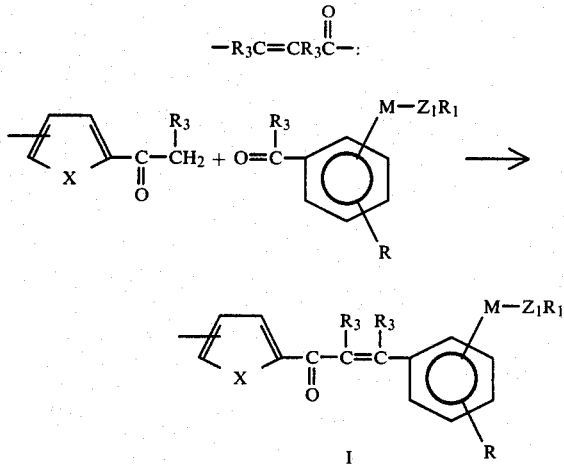

From the products thus formed, the corresponding secondary or tertiary alcohol ($Z{=}—R_3C{=}CR_3—CR_3OH—$) can be readily produced by reaction with a Grignard reagent ($R_3MgX$) to form the tertiary alcohol or reduction of the carbonyl to the secondary alcohol. Reduction of the double bond in Z produces the corresponding dihydrocompounds. Full reduction of the carbonyl, the alcohol (2° or 3°) or the unsaturated carbonyl or alcohol provides compounds in which Z is $(CHR_3)_{n'}$.

It is possible to pre-form appropriately substituted compounds of formula II by the same condensation reactions for compounds of formula I and then introduce the substituent $MZ_1R_1$ by known reactions e.g., Williamson reaction with the corresponding halo compound, acylation by Friedel-Crafts reaction, and the like with compounds of the following formula:

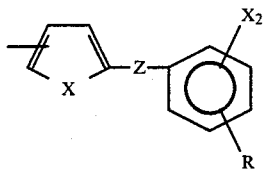

in which the substituent $X_2$ is H or halogen.

The present new compounds containing basic nitrogen can form salts with acids. All such acid salts are contemplated by the invention but especially preferred are salts with pharmaceutically acceptable acids, such as hydrochloric, sulfuric, nitric, toluenesulfonic, acetic, propionic, tartaric, malic and similar such acids well known in this art. Those compounds containing acid groups, such as the carboxyl group, can form salts with bases of which the preferred are the pharmaceutically-acceptable metal salts, e.g., Na, K. Ca and Mg salts.

The compounds of the present invention can be administered to the host in a variety of forms adapted to the chosen route of administration, i.e., orally, intravenously, intramuscularly or subcutaneous routes.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The following examples further illustrate the invention.

EXAMPLE 1

Preparation of 2-(3-phenoxycinnamoyl)pyrrole

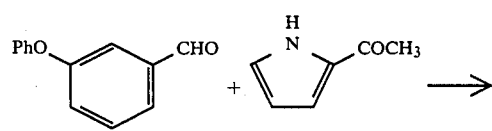

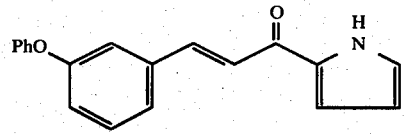

3

To a solution of 3.562 g (65 mmol) of 3-phenoxybenzaldehyde 1 and 7.313 g (65 mmol) of 2-acetylpyrrole 2 in 39 ml of ethanol was added 13 ml of 1N NaOH with stirring. After stirring at room temperature for 3.5 hours, the mixture was heated to reflux for 15 minutes and was then cooled. The reaction mixture was diluted to 500 ml with water and the precipitated solid product was filtered. The solid was washed copiously with water until the filtrate was neutral, followed by a hexane wash and then air dried to give 16.4 g of cream white solid product 3, m.p. 117°–120° C. Analytically pure material was prepared by recrystallization from isopropanol giving a white solid m.p. 120°–122° C.

EXAMPLE 2

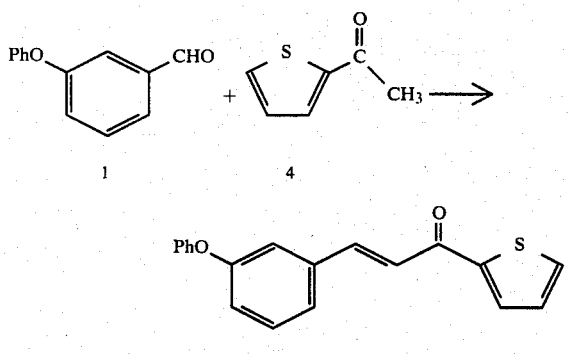

In a similar fashion, 2-(3-phenoxycinnamoyl)thiophene, m.p. 92°–94° C., was prepared.

EXAMPLE 3

Preparation of 2-(3-m-phenoxyphenylpropionyl)pyrrole

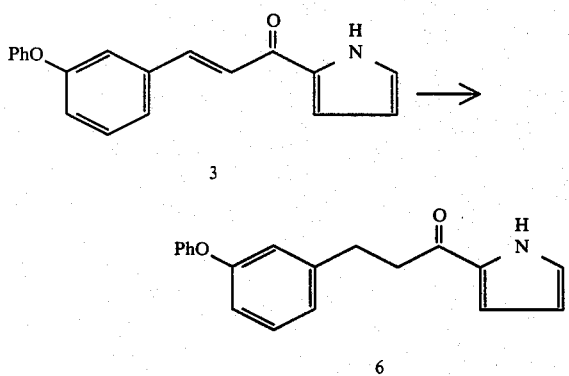

A mixture of 9 g (31.1 mmol) of 2-(3-phenoxycinnamoyl)pyrrole, 3, and 2 g of 10% Pd/C in 200 ml of ethanol was stirred and hydrogen gas was passed over the reaction mixture for 2 hours and 15 minutes. The mixture was dried and concentrated on a rotary evaporator to give 9 g of solid product. The crude reaction product was chromatographed on silica gel (for dry column chromatography), eluting with ethyl acetate/hexane (1:4). The chromatographed material was recrystallized twice from isopropanol yielding analytically pure light yellow solid material, m.p. 75°–76° C.

EXAMPLE 4

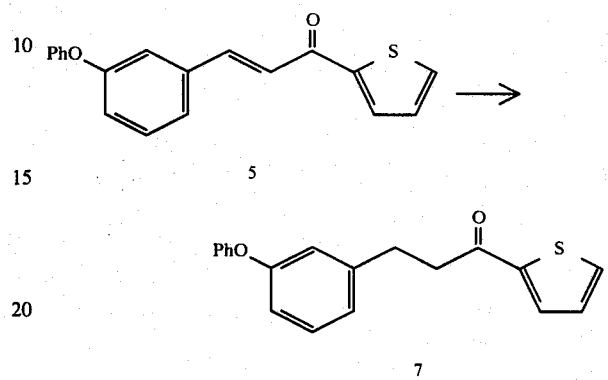

In a related fashion, 2-(3-(3-phenoxyphenyl)propionyl)thiophene, m.p. 73°–74° C. was prepared from 2-(3-phenoxycinnamoyl)thiophene, 5, with the following exceptions. The reaction was carried out at elevated pressures in a Parr hydrogenator (p. max. 59 psi), for extended periods of time, in a variety of solvent mixtures (ethyl acetate, ethanol, acetic acid, HCl), requiring several changes of catalyst and chromatographic purifications.

EXAMPLE 5

Preparation of 1-hydroxy-3-(2-phenoxyphenyl)-1-(2-pyrrolyl)propane

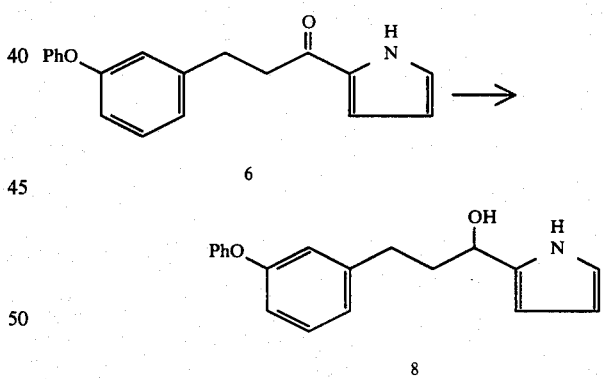

To a suspension of lithium aluminum hydride, 1.917 g (48 mmol) in 400 ml of ether under a nitrogen atmosphere was added dropwise in ethereal solution of the Example 3 product (7 g, 24 mmol, in 100 ml of ether) over a period of 30 min. After an additional 15 min. 1.9 g of water was added to the reaction mixture cautiously followed by 1.9 g of 15% w/w NaOH solution, and then followed by 5.7 g of water. After an additional 15 min. of stirring, anhydrous sodium sulfate was added. The mixture was stirred for 75 min. and the solids were filtered off and the filtrate was concentrated yielding an oil. The oil was dissolved in the minimum amount of ether and diluted with hexane. When the ether was distilled out, the product crystallized from the hexane, yielding after drying pure material m.p. 86°–88° C.

EXAMPLE 6

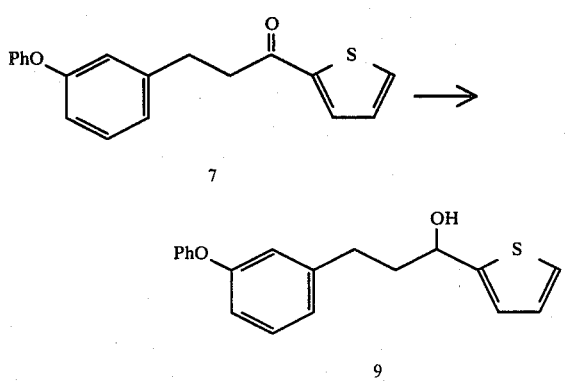

In a related fashion, 1-hydroxy-3-(3-phenoxyphenyl)-1-(2-thienyl)propane was prepared from the Example 4 compound by reduction with sodium borohydride in ethanol. The product was a liquid.

EXAMPLE 7

Preparation of 3-(3-phenoxyphenyl)-1-(2-pyrrolyl)propane

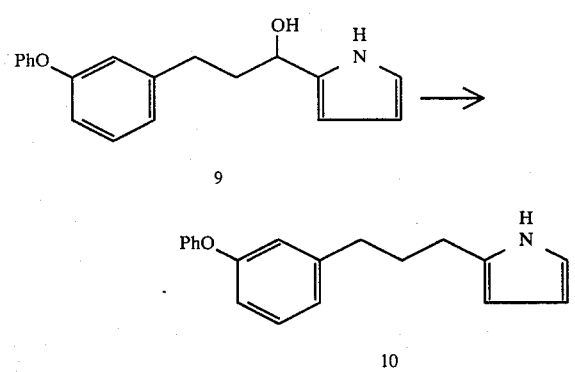

To a slurry of lithium aluminum hydride 1.0892 g (27.3 mmol) in 200 ml of ether under a nitrogen atmosphere, a solution of 2 g (6.82 mmol) of 1-hydroxy-3-(3-phenoxyphenyl-1-(2-pyrrolyl)propane, dissolved in ether was added over a period of 5 min. The mixture was stirred at room temperature for 19 hours and then refluxed for an additional 75 min. The mixture was cooled in an ice bath and 1 ml of water was added followed by 1 ml of 15% w/w NaOH solution followed by 3 ml of water. The mixture was stirred for 30 min. The solids were filtered off and the filtrate was evaporated to dryness yielding 2 g of amber oil. After three chromatographic runs (on silica gel for dry column chromatography), in which the eluants were mixtures of ethyl acetate and hexane, 1.26 g of pure product 10 was obtained as an oil.

EXAMPLE 8

4-Phenoxyphenyl-2-(2-furylvinyl)ketone

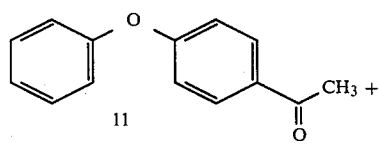

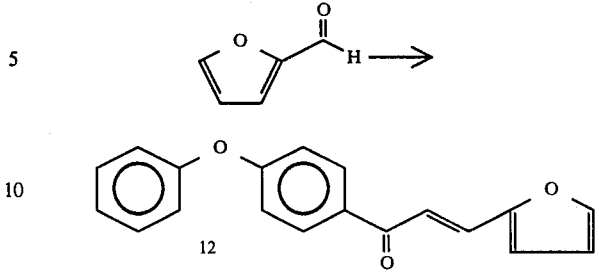

A mixture of 4.2 g of 4-phenoxyacetophenone and 2 g of 2-furfural was added to an alcoholic NaOH solution (1 g of NaOH in 7 ml of H₂O and 10 ml of EtOH). The reaction mixture was stirred at room temperature for 3 hours and was then diluted with H₂O. The precipitated product was then filtered to give 6 g of 12 as yellow solid product.

EXAMPLE 9

2,2-(4-Phenoxyphenyl)-3-(2-tetrahydrofuranyl)-1-propanol

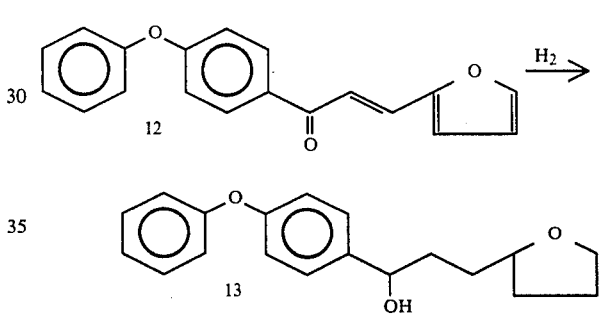

The compound 12 (5 g) and 1 g of 5% Pd/C in 100 ml of EtOH was hydrogenated at 15 psi overnight. After filtration, solvent was evaporated and the residue was purified by dry column chromatography to give 3.8 g of 13 as an oil.

EXAMPLE 10

5-(4-Benzyloxyphenyl)-1-(methyl-2-pyrrolyl)pentane

A. To a mixture of [2-(1-methyl-2-pyrrolyl)ethyl]-2-triphenylphosphonium bromide (0.1 mole) is added 0.1 mole of n-butyl lithium solution. After 0.5 hours, a solution of 3-(4-benzyloxyphenyl)propionaldehyde is added. After one hour of stirring, the mixture is filtered to remove triphenylphosphine oxide; it is then transferred to a separatory funnel, and washed with water followed by brine.

B. The etherate containing 5-(4-benzyloxyphenyl)-1-(1-methyl-2-pyrrolyl)pent-2-ene is dried with magnesium sulfate, filtered and evaporated to dryness. The residue is dissolved in 100 ml of ethanol and mixed with 2 g of 10% Pd/C and is hydrogenated at less than 10 psi for 2 hours. The catalyst is filtered off and the solvent is evaporated yielding the title compound.

The compounds of the present invention have potent activity in regulating the formation of lipoxygenease and as such possess therapeutic value in the treatment of inflammatory conditions and allergic responses such as anaphlaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygeneases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 5, 12-diHETE are chemotactic for human neutrophils and eosinophils, and may augment the inflammation process. 5-HPETE is known to be a precursor of slow-reacting substance of anaphylaxis (SRS-A). The SRS family of molecules, such as leukotrienes B, C, and D, have been shown to be potent bronchoconstrictors. (see, NATURE 288, 484–486 (1980)).

The following protocol describes an assay to detect inhibitors of the lipoxygenase pathway. Such inhibitors are believed to be capable of modulating the biosynthesis of the leukotrienes, a property believed to be useful in treating asthma and inflammatory disease states.

PROTOCOL FOR DETECTING INHIBITORS OF THE LIPOXYGENASE PATHWAY

A suspension of rat neutrophils in buffer is incubated for 3 minutes at 30° C. with [$^{14}$C]-arachidonic acid (AA) and Calcium Ionophore A23187. Citric acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform an an aliquot is spotted on silica gel TLC sheets, which are developed with an ethyl acetate/isooctane/water acetic acid solvent system. The 5-HETE spots are visualized with iodine, cut out and placed in scintillation vials for counting. After adjusting for the extraction efficiency, the amount (pmole) of [$^{14}$C]-5-HETE in each of the tubes is quantitated. The net pmoles of 5-HETE are obtained by subtracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

Table I provides the results of testing of compounds of the invention as lipoxygenase inhibitors (LOX):

TABLE I

| PRODUCT OF EXAMPLE | LOX |
|---|---|
| 1 | M |
| 2 | $I_{50} = 4.5 \mu M$ |
| 3 | $I_{50} = 2.5 \mu M$ |
| 4 | $I_{50} = 3.5 \mu M$ |
| 5 | $I_{50} = 6.5 \mu M$ |
| 6 | $I_{50} = 4.2 \mu M$ |
| 7 | $I_{50} = 4.5 \mu M$ |
| 9 | $I_{50} = 10 \mu M$ |

M = moderate activity at level tested.

What is claimed is:

1. A compound having anti-inflammatory and anti-allergic properties of the formula

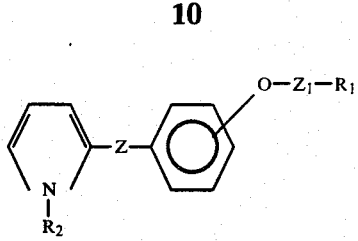

and pharmaceutically acceptable salts thereof, wherein Z is

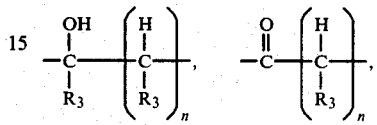

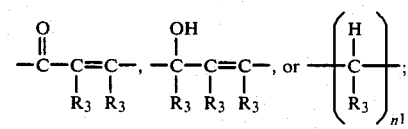

$R_1$ is phenyl or naphthyl;
$R_2$ is H or lower alkyl;
$R_3$ is H or $CH_3$;
n is 0, 1, 2, or 3; and
$n^1$ is 1, 2, or 3.

2. A compound of the formula

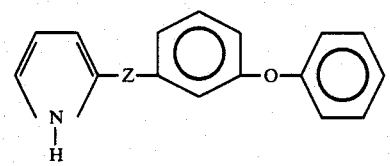

and pharmaceutically acceptable salts thereof; wherein Z is

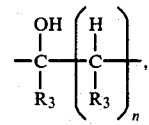

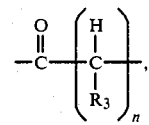

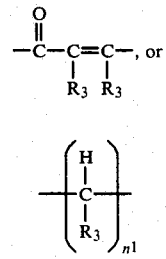

wherein
$R_3$ is H or $CH_3$;

n is 0-3; and n¹ is 1-3.

3. 2-(3-Phenoxycinnamoyl)pyrrole.

4. 2-(3-m-Phenoxyphenylpropinoyl)pyrrole.

5. 1-Hydroxy-3-(2-phenoxyphenyl)-1-(2-pyrrolyl)propane.

6. 3-(3-Phenoxyphenyl)-1-(2-pyrrolyl)propane.

7. 5-(4-Benzyloxyphenyl)-1-(1-methyl-2-pyrrolyl)pentane.

8. A therapeutic composition comprising as an active ingredient 50 to 300 mg of a compound according to claim 1 and a pharmaceutical carrier therefor.

* * * * *